United States Patent [19]
Shimada et al.

[11] Patent Number: 5,989,844
[45] Date of Patent: Nov. 23, 1999

[54] METHOD FOR EVALUATING DRUG METABOLISM AND REAGENT COMPOSITIONS THEREFOR

[75] Inventors: Kaoru Shimada, Kariya; Mayumi Mizutani, Handa; Fumiharu Naganeo, Chitagun, all of Japan

[73] Assignee: Pfizer Inc., New York, N.Y.

[21] Appl. No.: 09/132,974

[22] Filed: Aug. 12, 1998

[30] Foreign Application Priority Data

Aug. 13, 1997 [WO] WIPO ............... PCT/IB97/00988

[51] Int. Cl.$^6$ ............... C12Q 1/26; C12Q 1/00; C12Q 1/02
[52] U.S. Cl. ............... 435/25; 435/4; 435/29; 435/176; 435/177; 435/968; 435/963; 435/370; 435/366; 424/9.2
[58] Field of Search ............... 435/25, 4, 29, 435/176, 177, 968, 963, 370, 366; 424/9.2

[56] References Cited

U.S. PATENT DOCUMENTS

| | | | |
|---|---|---|---|
| 5,240,831 | 8/1993 | Barnes | 435/25 |
| 5,478,723 | 12/1995 | Parkinson et al. | 435/25 |
| 5,525,482 | 6/1996 | States et al. | 435/25 |

*Primary Examiner*—Louise N. Leary
*Attorney, Agent, or Firm*—Peter C. Richardson; Gregg C. Benson; Robert F. Sheyka

[57] ABSTRACT

This invention relates to a method for evaluating the susceptibility of pharmaceutical drugs to metabolism by a specific cytochrome P-450 isozyme, which comprises contacting the sample compound with a reagent composition prepared by adding the specific cytochrome P-450 isozyme to liver microsomes lacking said specific cytochrome P-450 isozyme in a carrier material. More particularly, this invention relates to a useful in vitro quantitative assay for drug metabolism by P-450 isozymes such as CYP2D6, CYP2C19, and CYP2A6. This invention also relates to a reagent composition which is useful for said in vitro assay.

13 Claims, 8 Drawing Sheets

7-Ethoxycoumarin

7-Ethoxycoumarin

Nifedipine

Nifedipine $y = -0.031x + 0.953 \quad r^2 = 0.279$

Propranolol

Propranolol y = 7.784x - 3.163   r² = 0.962

Yohinbine

Yohinbine y = 5.344x - 1.797   r² = 0.990

α-naphtoflavone

Nifedipine

METHOD FOR EVALUATING DRUG METABOLISM AND REAGENT COMPOSITIONS THEREFOR

TECHNICAL FIELD

This invention relates to a method for evaluating the susceptibility of pharmaceutical drugs to metabolism by cytochrome P450 isozymes in vitro, and a reagent composition for use in the evaluation of drug metabolism. More particularly, this invention provides a useful in-vitro quantitative assay for drug metabolism by P450 isozymes such as CYP2D6, CYP2C19, and CYP2A6.

BACKGROUND ART

Drug metabolism is an important factor in development of drugs. Especially, deficiency of drug metabolism in a body causes severe side effects such as exaggerated pharmacological response and toxic response.

Previous studies have revealed that cytochrome P-450 isozymes are responsible for drug metabolism, and oxidation by P-450 isozymes is a common aspect of the overall clearance of drugs. Further studies have revealed that genetic polymorphism of cytochrome P-450 isozymes underlies a wide spectrum of substrates specificity in drug oxidation. In certain cases, genetic mutation and/or deletion of one critical isozyme gene results in a significant alteration of a phenotype projected on substrate specificity. More specifically for example, defect of CYP2D6 gene is known to be responsible for poor metabolism of debrisoquine or spateteine (for example, H. J. Dengler et al., Arzenmittel-Forshung, Vol. 27, pp. 1836-, 1977). In addition, it has been reported that CYP2D6 oxidizes more than 30 drugs (for example, M. Eichelbaum et al., Pharmacol. Ther., Vol. 46, pp. 377-, 1990). Thus, those who have homozygous alteration in this recessive gene, are so-called "poor metabolizers (PMs)" and may suffer from severe side effects due to poor metabolism of drugs (for example, see M. Eichelbaum et al., Pharmacol. Ther., Vol. 46, pp. 377-, 1990). Such genetic alterations occur at rates of from 1 to 30% in different ethnic populations (for example, L. M. Distlerath et al., J. Biol. Chem., Vol. 260, pp. 9057-, 1985).

Previously, drug metabolism was evaluated by adding quinidine to a buffer solution of a substrate and microsomes (F. Peter et al., Molecular Pharmacology, Vol. 30, pp. 287–295, 1986). In this assay, quinidine is a strong competitive inhibitor of CYP2D6, and thus the contribution of CYP2D6 to the oxidative metabolism can be evaluated. However, quinidine is reported to inhibit other P-450 isozymes such as CYP3A4 (for example, F. P. Guengerich et al., Molecular Pharmacology, Vol. 30, pp. 287-, 1986), thereby preventing accurate evaluation of contribution of CYP2D6 in drug metabolism.

Therefore, it would be desirable if there were provided an improved method for accurately evaluating the susceptibility of a sample compound to metabolism with respect to a specific P-450 isozyme.

BRIEF DISCLOSURE OF THE INVENTION

The present invention provides a method for evaluating the susceptibility of a sample compound to metabolism with respect to a specific cytochrome P-450 isozyme, which comprises contacting the sample compound with a reagent composition prepared by adding said specific cytochrome P-450 isozyme to liver microsomes lacking said specific cytochrome P-450 isozyme in a carrier material. The method may further comprise (a) incubating a mixture of the sample compound and the reagent composition; (b) extraction of the reaction mixture obtained in Step (a); and (c) analyzing the reaction products isolated in Step (b). For the purposes of quantitating the assay, a plurality of the reagent compositions having different amount of the specific P-450 isozyme may be subjected to Step (a) to (c), respectively. The specific P-450 isozyme to be used in the method may be selected from CYP2D6, CYP2C19, CYP2A6, CYP1A1 and CYP2E1.

The present invention also provides a reagent composition for use in evaluating drug metabolism by a specific cytochrome P-450 isozyme, which comprises a liver microsome lacking said specific P-450, said specific P-450 isozyme and a carrier material. The liver microsome may be of human source lacking CYP2D6, CYP2C 19, or CYP2A6. The CYP2D6 isozyme, CYP2C 19 isozyme, and CYP2A6 isozyme to be added may be a recombinant CYP2D6-expressing microsome, a recombinant CYP2C 19-expressing microsome, or a recombinant CYP2A6-expressing microsome. The reagent composition may comprise more than one kind of PM microsomes.

According to the present invention, there can be provided a reagent composition and a method for accurately quantitating the contribution of certain P-450 isozymes such as CYP2D6, CYP2C 19, and CYP2A6 in drug metabolism.

DETAILED DESCRIPTION OF THE INVENTION

Figure 1A:
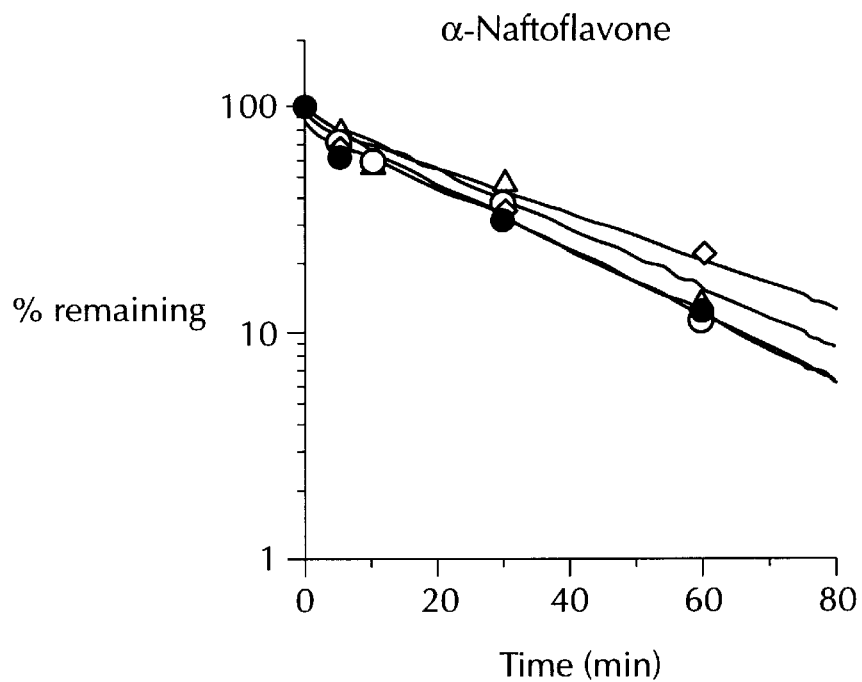
FIGS. 1A to 1L show drug metabolism mediated by CYP2D6. Closed circles indicate control treatment. Open diamonds indicate treatment with 0.1 (mg/ml) of a recombinant CYP2D6. Open circles indicate treatment with 0.5 (mg/ml) of a recombinant CYP2D6. Open triangles indicate treatment with 1.0 (mg/ml) of a recombinant CYP2D6.
Figure 1B:
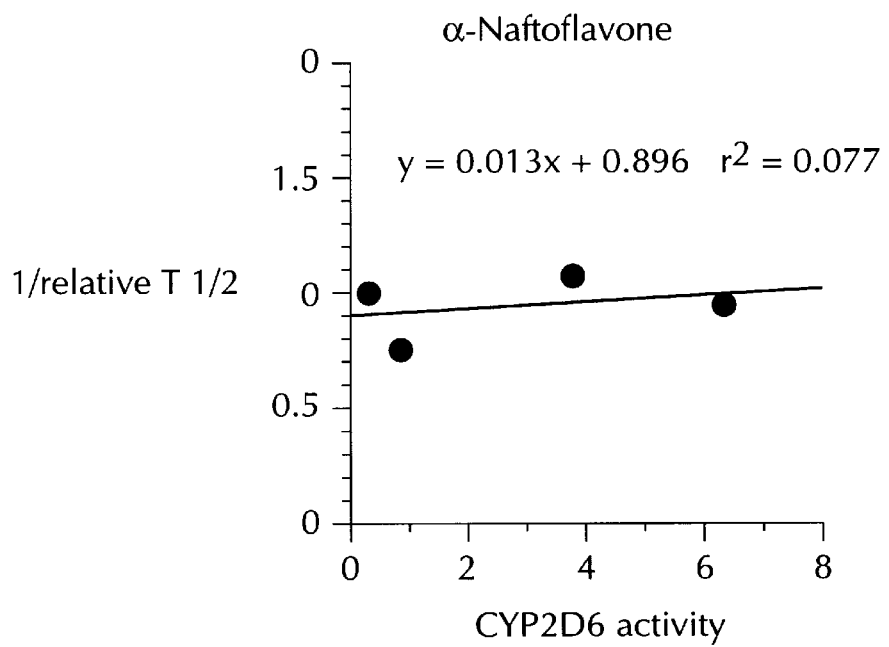
Figure 1C:
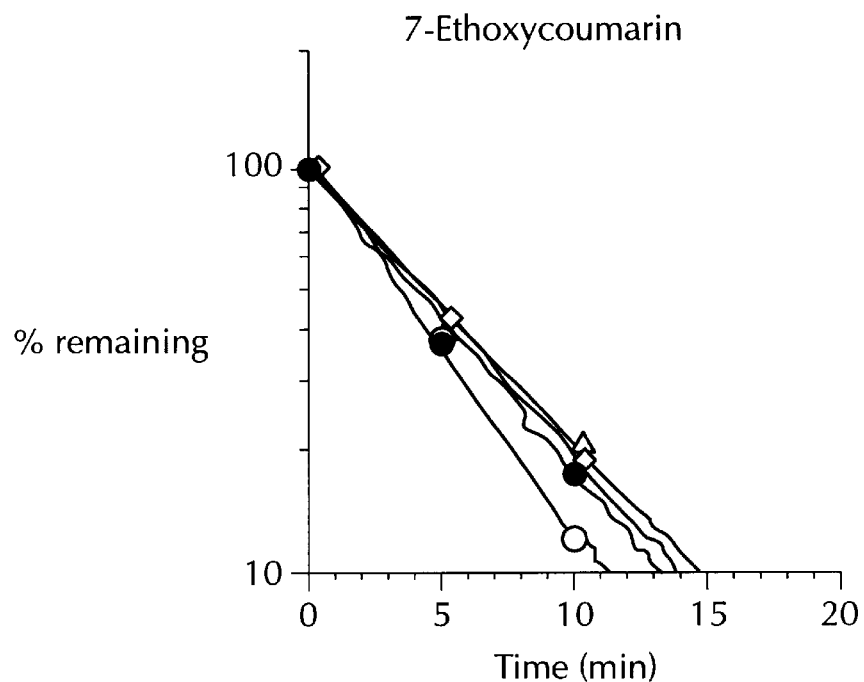
Figure 1D:
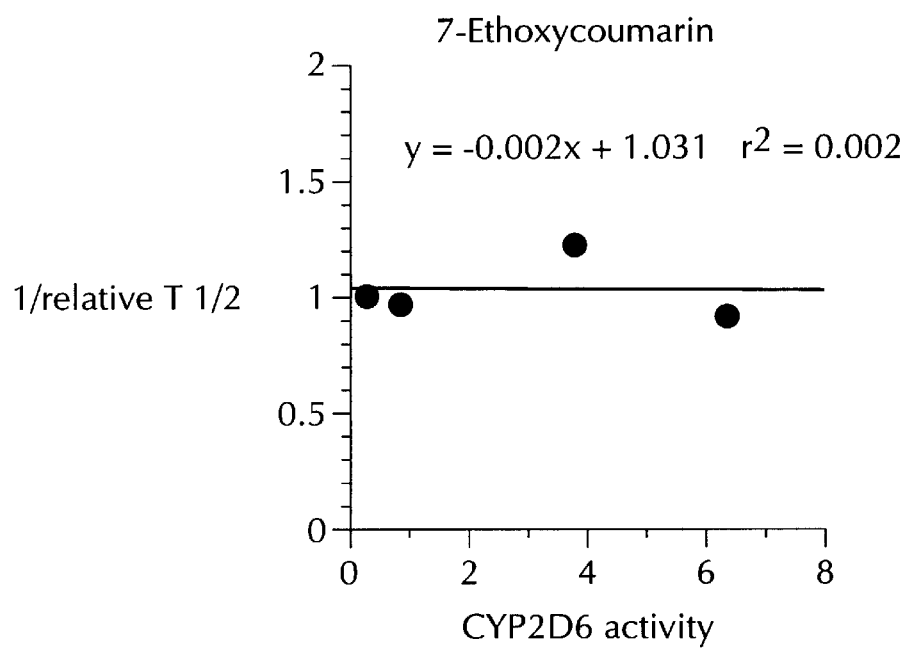
Figure 1E:
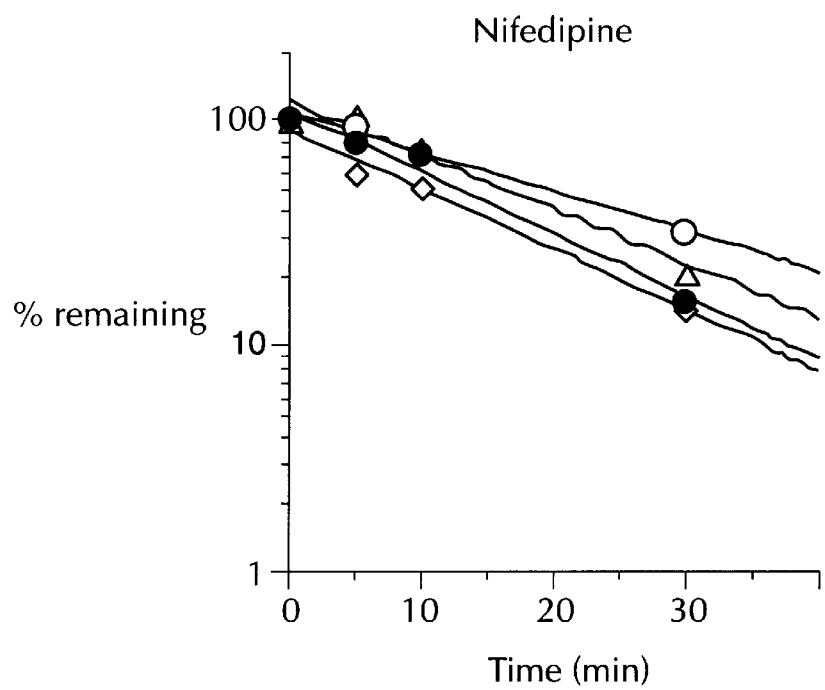
Figure 1F:
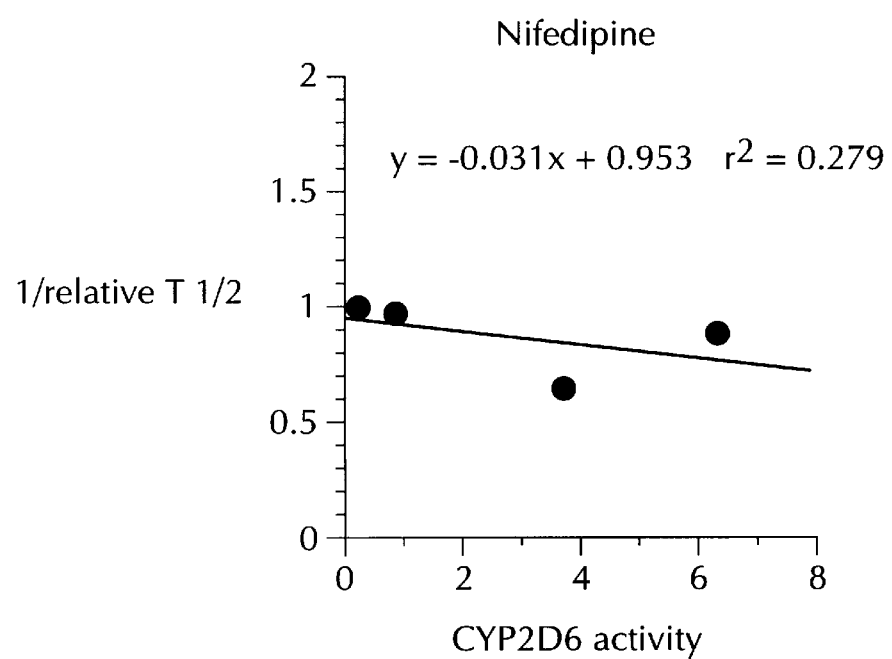
Figure 1G:
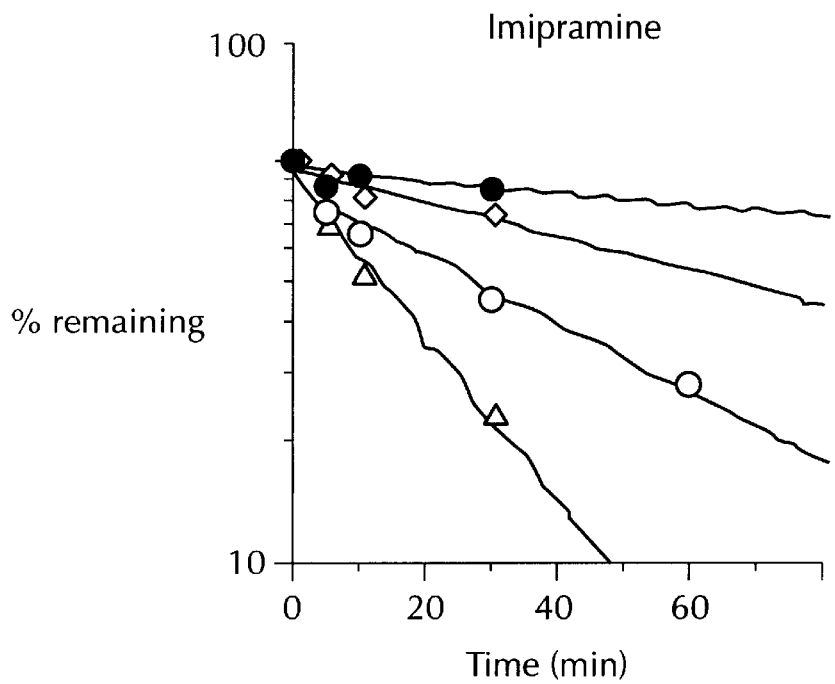
Figure 1H:
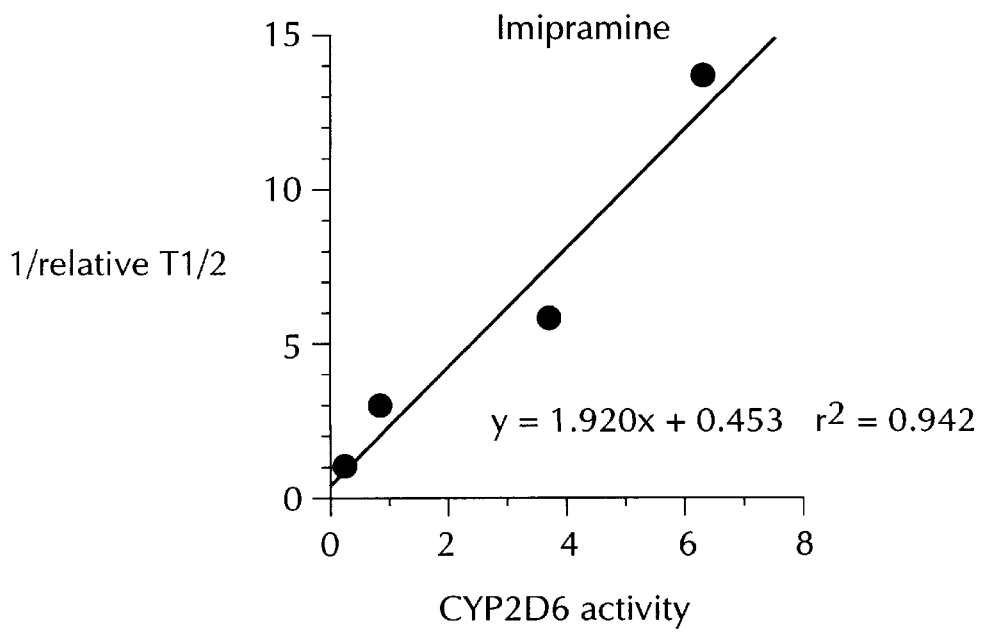
Figure 1I:
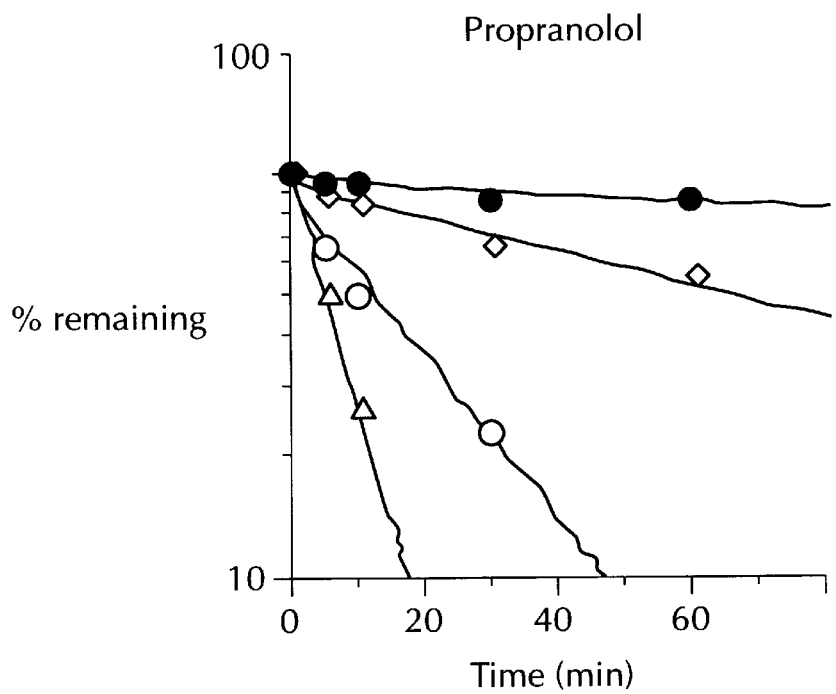
Figure 1J:
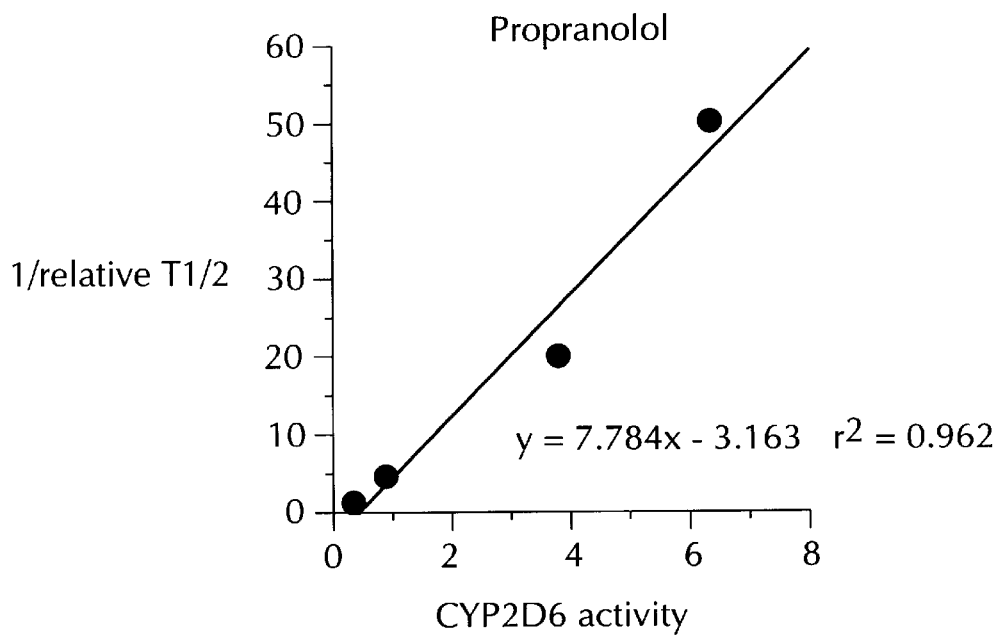
Figure 1K:
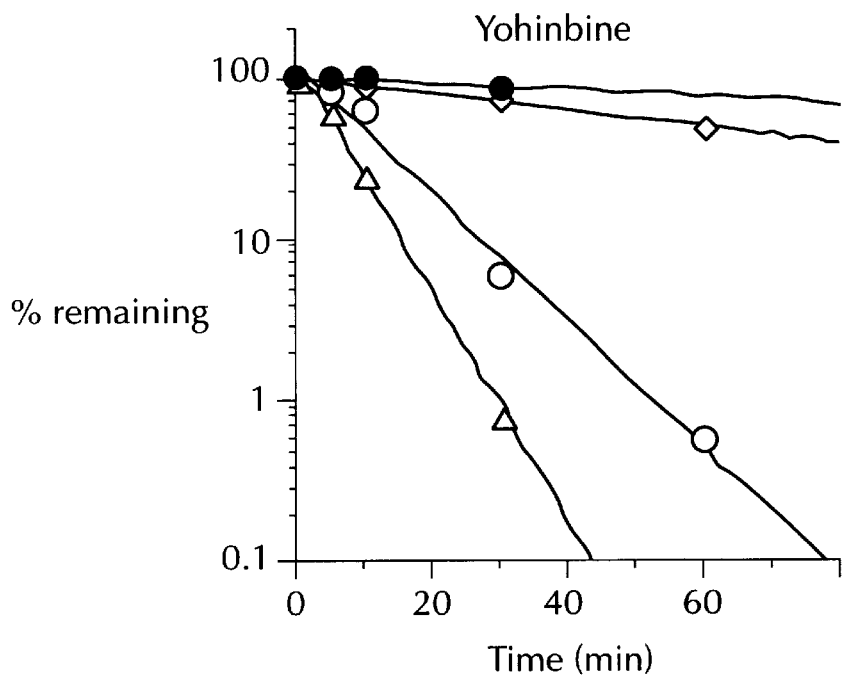
Figure 1L:
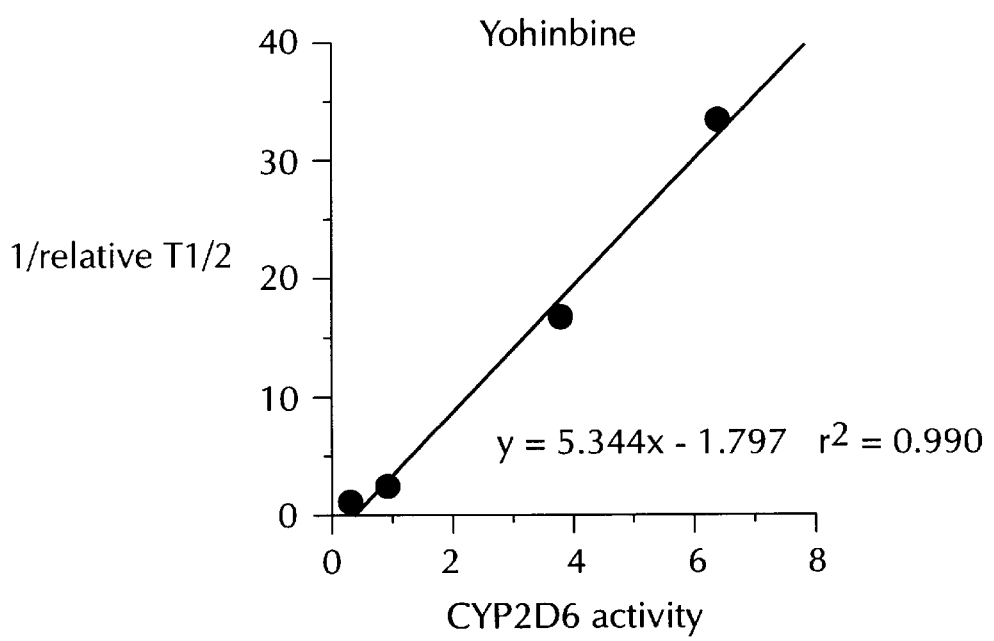
Figure 2A:
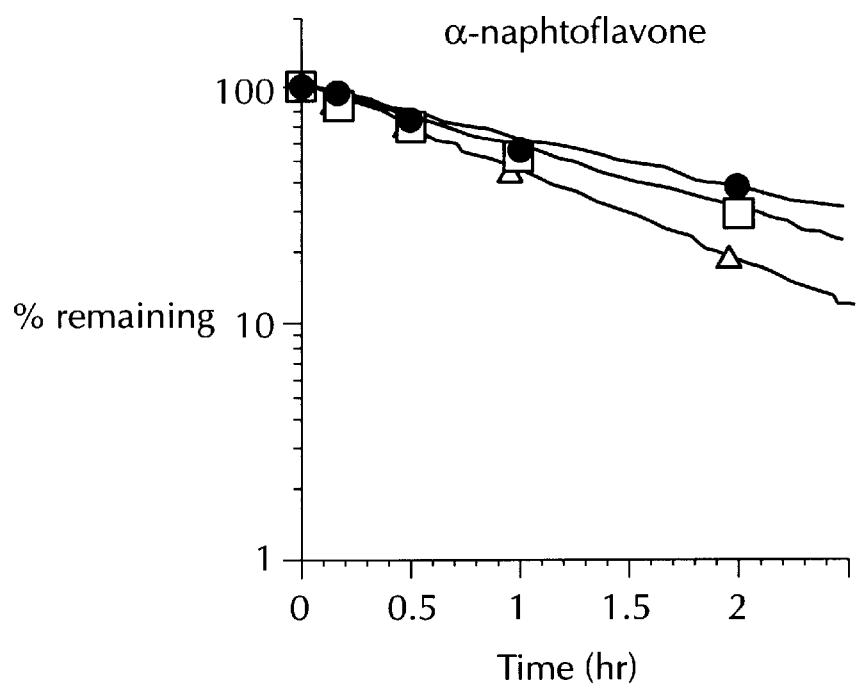
FIGS. 2A to 2D show drug metabolism mediated by CYP2C19. Closed circles indicate control treatment. Open squares indicate treatment with 0.1 (mg/ml) of a recombinant CYP2C19. Open triangles indicate treatment with 0.3 (mg/ml) of a recombinant CYP2C19.
Figure 2B:
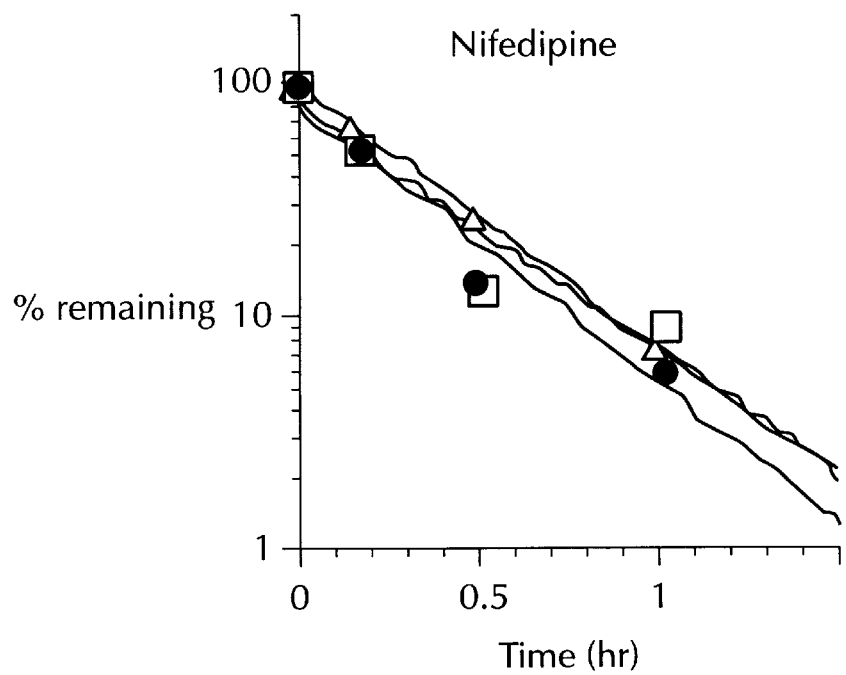
Figure 2C:
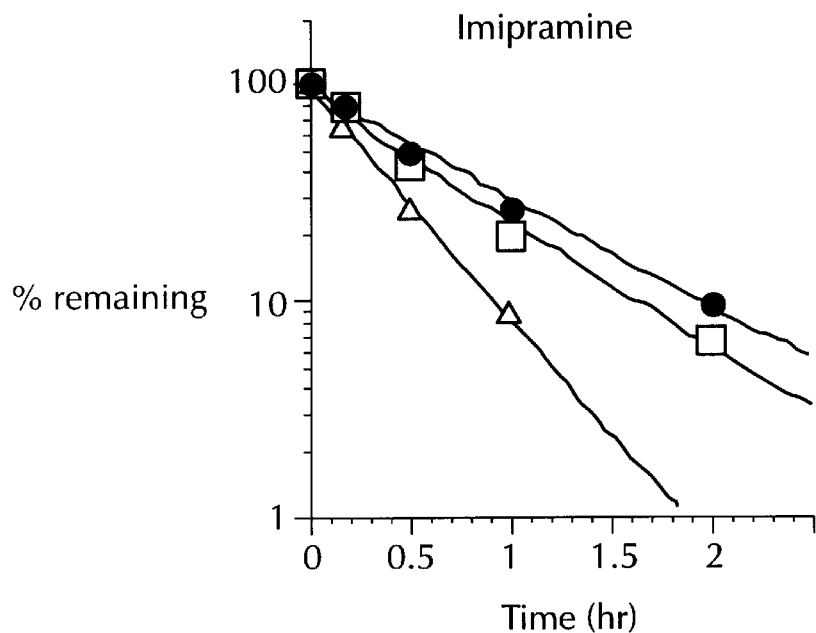
Figure 2D:
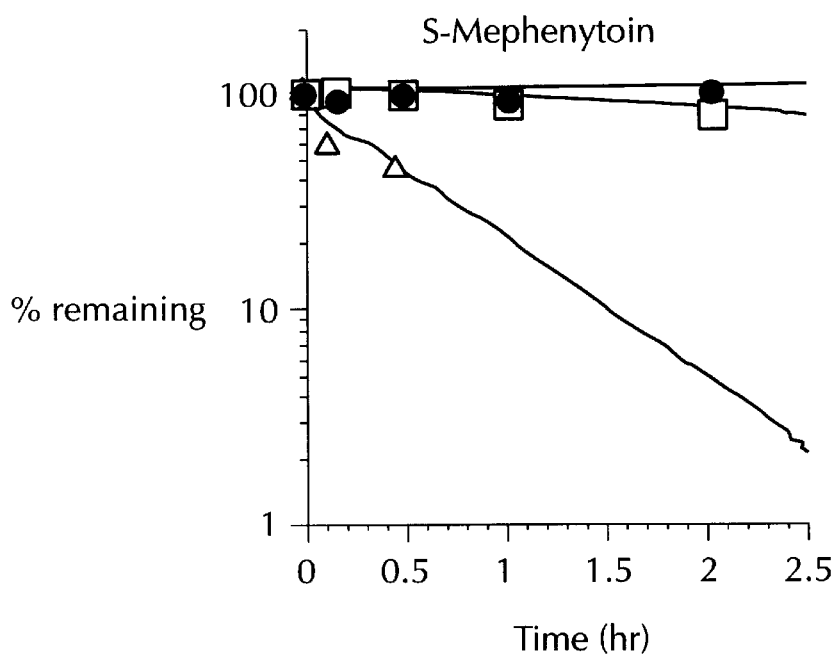

As used herein, "1'-hydroxy bufuralol generation activity" means the activity of hydroxylation of bufuralol (i.e., α-[[(1,1-dimethylethyl)amino]methyl]-7-ethyl-2-benzofuranmethanol), as measured by an analyzing method comprising HPLC (high pressure-liquid chromatography) and FLD (Fluorescence detector).

As used herein, "S-mephenytoin hydroxylation activity" means the activity of 4'hydroxylation of S-mephenytoin as measured by HPLC-MS.

The present invention will be described in more detail below.

In the method of the present invention, firstly, a reagent composition is prepared by adding a specific cytochrome P-450 isozyme to a liver microsome lacking said specific cytochrome P-450 isozyme in a carrier material. The specific cytochrome P-450 isozyme to be selected is an isozyme whose influence on metabolism of a sample compound should be investigated. Such P-450 isozyme may be CYP2D6, CYP2C19, CYP2A6, CYP1A1 or CYP2E1. Suitable carrier materials include, for example, $MgCl_2$, G-6-P (glucose-6-phosphate), G-6-PDH(glucose-6-phosphate dehydrogenase), NADP(nicotinamido adenine dinucleotide phosphate), NADH (reduced nicotinamido adenine dinucleotide), $K_2HPO_4$ $Na_2HPO_4$, $KH_2PO_4$, and $NaH_2PO_4$.

In one embodiment of the reagent composition according to the present invention, the liver microsome to be used may be of human source lacking CYP2D6, CYP2C19, or CYP2A6. In this case, the P-450 isozyme to be contained in the reagent composition is CYP2D6, CYP2C19, or CYP2A6. Human liver microsomes lacking a specific P-450 isozyme are commercially available, for example, from Keystone Skin Bank, USA. A preferred human liver microsome lacking a CYP2D6 isozyme may be HHM-0116 and HHM-0113 (Keystone Skin Bank). A preferred human liver microsome lacking a CYP2C19 isozyme may be HHM-0120 or HHM-0140 (Keystone Skin Bank). A preferred human liver microsome lacking a CYP2A6 may be HHM-0110 or HHM-0146(Keystone Skin Bank).

As used herein, the CYP2D6-lacking microsome may be considered to have a 1'-hydroxy bufuralol generation activity of up to 2.0 (pmol/min/mg), preferably up to 0.7 (pmol/min/mg) when bufuralol is used at 10 $\mu$M as a substrate. The CYP2C19-lacking microsome may be considered to have a S-mephenytoin hydroxylation activity of up to 5 (pmol/min/mg), preferably up to 1.7 (pmol/min/mg) when S-mephenytoin is used at 100 $\mu$M as a substrate. The CYP2A6 lacking microsome may be considered to have a coumarin 7-hydroxylation activity of up to 0.2 (nmol/mg/min.) preferably up to 0.1 (nmol/mg/min.) However, it should not be construed that the above-mentioned ranges limit the scope of the present invention.

As the specific P-450 isozymes, recombinant microsomes may preferably be used. In a preferred embodiment, microsomes expressing a recombinant CYP2D6, CYP2C19, or CYP2A6 may be used. Such recombinant microsomes are commercially available from, for example, Gentest, USA; Wako Pure Chemical Industries Ltd., Japan; and Sumitomo Chemical, Japan.

It is difficult to clearly define the threshold value between CYP2D6, CYP2C19, or CYP2A6 activities in the microsome obtained from PM, and the corresponding activity in the microsome obtained from a normal metabolizer. Thus, the antibody specific for the CYP2D6, CYP2C19, or CYP2A6 isozyme can be added to the reaction mixture for inhibiting the activity of the CYP2D6, CYP2C19, or CYP2A6 which may be present in the used PM microsome.

More specifically, when a metabolism activity of a sample compound is to be evaluated with respect to CYP2D6, a CYP2D6-lacking liver microsome is selected as a liver microsome lacking a specific cytochrome P-450 isozyme. Then, a series of different amount (e.g., from 0 to 1.0 mg/ml) of a recombinant CYP2D6-expressing microsome may be added to the same amount of CYP2D6-lacking liver microsome in a carrier material such as $MgCl_2$, G-6-P, G-6-PDH, NADP, NADH, $K_2HPO_4$, $Na_2HPO_4$, $KH_2PO_4$, $NaH_2PO_4$ to prepare a predetermined number of reagent composition solutions having different amount of CYP2D6 isozyme.

The reagent composition solutions may be buffered by addition of potassium phosphate buffer to a pH within the range of 6 to 8, preferably 7.2 to 7.6. If desired, a control microsome can be added to maintain a desired protein concentration. In the present invention, the reagent composition may comprise 0.1 to 10, more preferably 0.5 to 3.0 weight/volume percent of the human liver microsome; 0.01 to 5.0, more preferably 0.2 to 1.0 weight/volume percent of CYP2D6 or CYP2C19. The range depends on the activity of CYP2D6 or CYP2Cl9 used. If desired, the other additives such as internal standards may be added to the reagent composition.

Then, after pre-incubation to equilibrate the reagent compositions, a sample compound is added to the reagent composition. The mixture of the sample compound and the reagent composition may be subjected to incubation. The incubation may be conducted in the presence of NADP, NADH, G-6-P, G-6-PDH or a mixture thereof. The incubation may be conducted at a temperature of 35 to 38 °C., preferably from 36.5 to 37.5 °C. The incubation time may range from 0 to 300 minutes, more particularly from 0 to 120 minutes. The reaction mixture may be stirred.

Then, the reaction products may be isolated from the reaction mixture by a standard technique such as extraction and centrifugation. Preferably, the internal standard can be added to an aliquot of a sample withdrawn from the reaction mixture. The internal standards can be difflused or solved in an appropriate solutions such as acetonitrile (ACN). Preferably, the mixture in a solvent may be stirred and sonicated. The preferred stirring condition may be in the range of 200×g to 6,000×g by a conventional centrifuge for 1 minute to 30 minutes.

Finally, the reaction products obtained are analyzed. The preferred quantitative analysis methods for substrates and products in each assay include a mass spectrometer linked with a HPLC (high performance liquid chromatography). The analysis of the reaction products may give evaluation of metabolism activities of the sample compounds with respect to specific P-450 isozymes.

EXAMPLES

The present invention is illustrated by, but not limited to the details the following examples.

EXAMPLE 1

Characterization of P-450 isozymes

The PM microsomes used in the following examples are HHM-0 116, HHM-0113, HHM-0102, HHM-0140, HHM-0110, and HHM-0146. The characterization of the PM microsomes are summarized in Table 1 (this table is cited from the list of Keystone Skin Bank (December 1995)).

TABLE 1

Characterization of P-450 Isozyme Activities in Human Liver Microsome

| Lot. # | Protein[a] | P-450[b] | P-450 reductase[c] | ECOD Mix[d] | CYP 1A2[e] | CYP 2A6[f] |
|---|---|---|---|---|---|---|
| HHM-0113 | 18 | 0.68 | 44 | 207 | 839 | 1.16 |
| HHM-0116 | 16 | 0.31 | 64 | 266 | 500 | 1.83 |
| HHM-0102 | 18 | 0.31 | 56 | 141 | 293 | 1.29 |
| HHM-0140 | 24 | 0.37 | 53 | 292 | 310 | 1.10 |
| HHM-0110 | 14 | 0.24 | 47 | 44 | 394 | 0.04 |
| HHM-0146 | 29 | 0.26 | 70 | 180 | 225 | 0.05 |
| Mean of 162 microsomes | 20.6 | 0.4 | 61.3 | 261 | 496 | 1.2 |
| Stdev* | 4.3 | 0.1 | 14.8 | 175 | 262 | 1.1 |

TABLE 1-continued

Characterization of P-450 Isozyme Activities in Human Liver Microsome

| Lot. # | CYP 2C[g] | CYP 2D[h] | CYP 2E[i] | CYP 3A[j] | CYP 4A[k] |
|---|---|---|---|---|---|
| HHM-0113 | 51 | 51 | 1972 | 4.2 | 2.5 |
| HHM-0116 | 16 | 79 | 1320 | 2 | 1.8 |
| HHM-0102 | 4 | 437 | 950 | 2.0 | 1.2 |
| HHM-0140 | 2 | 167 | 1225 | 2.6 | 1.3 |
| HHM-0110 | 138 | 113 | 1504 | 0.3 | 0.7 |
| HHM-0146 | 17 | 174 | 1058 | 2.8 | 0.6 |
| Mean of 162 microsomes | 46 | 526 | 1117 | 2.5 | 1.5 |
| Stdev* | 52 | 257 | 589 | 2.1 | 0.7 |

*Standard Deviation
[a] Protein refers to microsomal protein (mg/ml) as determined by the Pierce protein assay.
[b] P-450 was determined by the carbon monoxide spectrum (nmol/mg microsomal protein).
[c] Cytochrome P-450 reductase activity was determined by the rate of reduction at room temperature (nmol/mg/min).
[d] 7-ECOD activity was determined by the rate of 7-ethoxycoumarin O-deethylation (pmol/mg/min).
[e] Isozyme 1A2 activity was determined by the rate of phenacetin O-deethylation (pmol/mg/min).
[f] Isozyme 2A6 activity was determined by the rate of coumarin 7-hydroxylation (nmol/mg/min).
[g] Isozyme 2C activity was determined by the rate of mephenytoin 4-hydroxylation (pmol/mg/min).
[h] Isozyme 2D activity was determined by the rate of dextromethorphan O-demethylattion (pmol/mg/min).
[i] Isozyme 2E activity was determined by the rate of chlorzoxazone 6-hydroxylation (pmol/mg/min).
[j] Isozyme 3A activity was determined by the rate of fractional production of [$^{14}$C] 6β-hydroxy teststerone (nmol/mg/min).
[k] Isozyme 4A activity was determined by the rate of fractional production [$^{14}$C] omega-hydroxy lauric acid (nmol/mg/min).

EXAMPLE 2

Characterization of reagent compositions b 1'-hydroxy bufuralol generation activity The reagent compositions of this invention, PM microsomes (i.e., HHM-0116 and HHM-0113), normal human liver microsomes mixture (i.e., HLM mix-A and HLM mix-B), and the microsomes containing a mutant CYP2D6 in which the carboxy terminus is a methionine residue instead of a valine residue (i.e., CYP2D6-Met) were tested for 1'-hydroxy bufuralol generation activity according to above mentioned procedures for the evaluation of a metabolism activity. The results are shown in Table 2.

TABLE 2

1'-Hydroxy bufuralol Generation Activity

| test # | PM or Reagent Compositions of this Invention | 1'-Hydroxy bufuralol[1] Generation Activity (pmol/min/mol) |
|---|---|---|
| 1 | HHM-0116 + control microsome | 0.271 |
| 2 | HHM-0116 + 0.01 mg/ml-CYP2D6 | 0.293 |
| 3 | HHM-0116 + 0.1 mg/ml-CYP2D6 | 0.876 |
| 4 | HHM-0116 + 0.3 mg/ml-CYP2D6 | 2.059 |
| 5 | HHM-0116 + 0.5 mg/ml-CYP2D6 | 3.788 |
| 6 | HHM-0116 + 1.0 mg/ml-CYP2D6 | 6.370 |
| 7 | HHM-0113 + control microsome | 0.505 |
| 8 | HMM-0113 + 0.03 mg/ml-CYP2D6 | 0.580 |
| 9 | HHM-0113 + 0.3 mg/ml-CYP2D6 | 1.369 |
| 10 | HHM-0113 + 0.5 mg/ml-CYP2D6 | 2.810 |
| 11 | HHM-0113 + 1.0 mg/mlCYP2D6 | 3.426 |
| 12 | CYP2D6-Met2[2] | 6.566 |
| 13 | HLM mix-A3[3] | 3.828 |
| 14 | HLM mix-B3[3] | 2.220 |

[1] Bufuralol is a generally accepted as a substrate for P-450.
[2] CYP2D6-Met represents a mutant CYP2D6 whose carboxy terminus is a methionine residue.
[3] HLM mix-A and HLM mix-B represent separate combinations of liver microsomes, and each group contains five different human microsomes.

S-mephenytoin hydroxylation activities

The reagent compositions of this invention, PM microsome (i.e., HHM0102), normal human liver microsomes mixture (i.e., HLM mix-A, and HLM mix-B, and (CYP2C19 0.1 mg/ml) were tested for hydroxymephenytoin generation activity which is a known property of microsome obtained from a normal metabolizer.

HHM-0102 microsomes (1.0 mg protein/ml) were mixed with a total of 0.3 mg protein/ml of CYP2C19 microsomes and the control microsomes with various ratios. The microsome mixture was incubated with 100 μM S-(+)-Mephenytoin in the presence of 1.3 mM NADP, 0.9 mM NADH, 3.3 mM G-6-P, 3.3 mM MgCl$_2$, and G-6-PDH (8 units/ml) in a total volume of 0.48 ml of 100 mM potassium phosphate buffer, pH 7.4, at 37 °C. At specified incubation times (30, 60 min), an aliquot of 100 μl was withdrawn from the reaction mixture and mixed with 1 ml of acetonitrile (ACN) containing (2S,3S)-3-(2-methoxybenzylamino)-2-diphenylmethyl-1-azabicyclo[2,2,2]octane (50 ng/ml), an internal standard. Protein in the sample was precipitated by centrifugation (1,800×g for 10 min), and the resulting supernatant was taken. Hydroxy mephenytoin which was generated in samples were analyzed by LC/MS/MS. The results are summarized in Table 3.

TABLE 3

S-mephenytoin hydroxylation activities

| test # | PM or Reagent Compositions of this Invention | S-mephenytoin hydroxylation Activiy (pmol/min/mg) |
|---|---|---|
| 1 | HHM-0102 + control microsome | 0.1928 |
| 2 | HHM-0102 + 0.03 mg/ml-CYP2C19 | 15.125 |
| 3 | HHM-0102 + 0.1 mg/ml-CYP2C19 | 37.619 |
| 4 | HHM-0102 + 0.3 mg/ml-CYP2C19 | 84.770 |
| 5 | CYP2C19 0.1 mg/ml | 18.110 |
| 6 | HLM mix-A | 10.371 |
| 7 | HLM mix-B | 17.452 |
| 8 | HHM-0116 | 5.122 |
| 9 | HHM-0102 | 0.193 |
| 10 | HHM-0140 | 0.193 |

EXAMPLE 3

Evaluation of drug metabolism by CYP2D6 and CYP2C19 activities

Substrates

The substrates used in Working and Comparative Examples are ized in Table 4.

TABLE 4

Substrates Used in Working and Comparative Examples

| | | Substrates |
|---|---|---|
| a) CYP2D6-mediated metabolism | | |
| Working Examples | CYP2D6 substrate | imipramine, propranolol, yohinbine |
| Comparative Examples | CYP1A1 substrate | α-naftoflavone |
| | CYP3A substrate | nifedipine |
| | CYP2B substrate | 7-ethoxycoumarin |
| b) CYP2C 19-mediated metabolism | | |
| Working Examples | CYP2C19 substrate | S-(+)-mephenytoin, imipramine |
| Comparative Examples | CYP2D6 substrate | imipramine, yohinbine |
| | CYP1A1 substrate | α-naftoflavone |
| | CYP3A substrate | nifedipine |

Experimental Protocols a) CYP2D6-mediated metabolism

The substrates (1 μM) were incubated with PM human liver microsome HHM-0116, or HHM-0113 supplemented with a recombinant CYP2D6-expressing microsome (0–1.0 mg/ml) or control vector microsomes in the presence of 1.3 mM NADP, 0.9 mM NADH, 3.3 mM G-6-P, 3.3 mM $MgCl_2$ and 8 units/ml G-6-PDH respectively in a total volume of 1.2 ml of 100 mM potassium phosphate buffer. The pH of the solution was 7.4. The incubation temperature was 37° C. At specific incubation times (0, 5, 10, 30, 60 minutes), an aliquot of 100 μl was withdrawn from the reaction mixture and mixed with 1 ml of ACN containing 5 ng/ml (2S, 3S)-3-(2-methoxybenzylamino)-2-diphenylmethyl-1-azabicyclo[2,2,2] octane as an internal standard. Protein was subsequently precipitated by centrifugation (1,800×g for 10 min). and the resulting supernatant was taken, evaporated and dissolved in 100 μl of 60% ACN. Concentrations of substrates and products in the sample solutions were analyzed with a Sciex API-III mass spectrometer linked with a Hewlett-Packard HP1090 HPLC system. A volume of 10 μl of the sample portion was injected to the HPLC system equipped with a Tosoh ODS-80Ts column manufactured by Tosoh (3.2×15 mm). Mobile phases comprised 80% acetonitrile(ACN) and 10 mM ammonium acetate and the elution was isocratic with a flow rate of 0.2 ml/min. The effluent from the HPLC column was introduced into the atmospheric pressure ionization source via an ion spray interface with splitting the effluent. The ion spray interface was operated at 5000 volt in a positive ion mode. Collision gas (argon) thickness (CGT), curtain gas ($N_2$) and Neblizer gas (air) was $300 \times 10^{13}$ molecules/cm², 0.6 liter/minute and 40 PSI, respectively. The Q2 rod offset voltage (R2) was 0–6 V. The compounds were detected by multiple reacting monitoring (MRM) detection in the API-III mass spectrometer. The MS-MS were generally the combination of precursor and product. The MS/MS of 273/171, 191/163, 347/194, 281/208, 260/155, 355/144 and 413/121 was for α-naftoflavone, 7-ethoxycoumarin, nifedipine, imipramine, propranolol, yohinbine and (2S, 3S)-3-2-methoxybenzylamino)-2-diphenylmethyl-1-azabicyclo[2,2,2] octane. Concentrations of the remaining substrates in each sample solution (%-remaining) were plotted against the desired incubation times (FIG. 1(a), (c), (e), (g), (i), (k)). The values of $T_{1/2}$ were obtained in each graph, and the values are summarized in Table 5. The correlation of $1/T_{1/2}$ and CYP2D6 activity is also shown (FIG. 1 (b), (d), (f), (h), (j), (l)).

b) CYP2C 19-mediated metabolism

The HHM-0102 microsomes (1.0 mg protein/ml) were mixed with a total of 0.3 mg protein/ml of CYP2C19 microsomes and the control microsomes with various ratios. The microsome mixture was incubated with 1 μM of P450 substrates (i.e., α-naftoflavone, nifedipine, imipramine, S-(+)-mephenytoin, or yohinbine) in the presence of 1.3 mM NADP, 0.9 mM NADH, 3.3 mM G-6-P, 3.3 MM $MgCl_2$, and G-6-PDH (8 units/ml) in a total volume of 1.2 ml of 100 mM potassium phosphate buffer, pH 7.4, at 37° C. At specified incubation times (0, 10, 30, 60, 120 min), an aliquot of 100 μl was withdrawn from the reaction mixture and mixed with 1 ml of acetonitrile (ACN) containing (2S,3S)-3-(2-methoxybenzylamino)-2-diphenylmethyl-1-azabicyclo[2,2,2]octane (50 ng/ml), an internal standard. Protein in the sample was precipitated by centrifugation (1,800×g for 10 min), and the resulting supernatant was taken. Substrates in samples were analyzed by LS/MS/MS, in a Sciex API-III mass spectrometer linked with a Hewlett-Packard HP1090 HPLC system. A volume of 10 μl of the sample was injected to the HPLC system equipped with a Tosoh ODS-80Ts column (3.2×15 mm). Concentrations of the remaining substrates in each sample solution (%-remaining) were plotted against the desired incubation times (FIG. 2). The values of $T_{1/2}$ were obtained in each graph, and the values are summarized in Table 6.

c) CYP2A6-mediated metabolism

In a similar way, the HHM-0110 microsome (1.0 mg protein/ml) are mixed with CYP2A6 microsomes and the control microsomes with various ratio. The microsome mixture is incubated with 1 μM of P450 substrates (i.e., α-naftoflavone, nifedipine, imipramine, S-(+)-mephenytoin, coumarin, or yohinbine) in the presence of 1.3 mM NADP, 0.9 mM NADH, 3.3 mM G-6-P, 3.3 mM $MgCl_2$, and G-6-PDH (8 units/ml) in a total volume of 1.2 ml of 100 mM potassium phosphate buffer, pH 7.4, at 37° C. At specified incubation times (0, 10, 30, 60, 120 min), an aliquot of 100 μl is withdrawn from the reaction mixture and mixed with 1 ml of acetonitrile (ACN) containing (2S,3S)-3-(2-methoxybenzylamino)-2-diphenylmethyl-1-azabicyclo[2,2,2]octane (50 ng/ml), an internal standard. Protein in the sample is precipitated by centrifugation (1,800×g for 10 min), and the resulting supernatant is taken. Substrates in samples are analyzed by LS/MS/MS, in a Sciex API-III mass spectrometer linked with a Hewlett-Packard HP1090 HPLC system. A volume of 10 μl of the sample is injected to the HPLC system equipped with a Tosoh ODS-80Ts column (3.2×15 mm). Concentrations of the remaining substrates in each sample solution (%-remaining) are plotted against the desired incubation times. The values of $T_{1/2}$ can be obtained in each graph.

TABLE 5

T½ of P-450 substrates in CYP2D6-mediated drug metabolism

| Compounds | α-Naftoflavone | | | | 7-Ethoxycoumarin | | | |
|---|---|---|---|---|---|---|---|---|
| Protein (HHM0116 + 2D6)[1] | 0 (control microsome)[3] | 0.1 | 0.5 | 1.0 | 0 (control microsome)[3] | 0.1 | 0.5 | 1.0 |
| T½[2] | 0.36 | 0.48 | 0.34 | 0.38 | 0.07 | 0.07 | 0.05 | 0.07 |
| T$_{1/2}$ ratio (/control microsome) | 1.00 | 1.34 | 0.95 | 1.07 | 1.00 | 1.03 | 0.82 | 1.10 |

| Compounds | Nifedipine | | | | Imipramine | | | |
|---|---|---|---|---|---|---|---|---|
| Protein (HHM0116 + 2D6)[1] | 0 (control microsome)[3] | 0.1 | 0.5 | 1.0 | 0 (control microsome)[3] | 0.1 | 0.5 | 1.0 |
| T½[2] | 0.18 | 0.19 | 0.29 | 0.21 | 3.34 | 1.11 | 0.58 | 0.24 |
| T½ ratio (/control microsome) | 1.00 | 1.04 | 1.59 | 1.15 | 1.00 | 0.33 | 0.17 | 0.07 |

| Compounds | Propranolol | | | | Yobinbine | | | |
|---|---|---|---|---|---|---|---|---|
| Protein (HHM0116 + 2D6)[1] | 0 (control microsome)[3] | 0.1 | 0.5 | 1.0 | 0 (control microsome)[3] | 0.1 | 0.5 | 1.0 |
| T½[2] | 5.02 | 1.17 | 0.25 | 0.09 | 2.18 | 0.98 | 0.13 | 0.Q7 |
| T½ ratio (/control microsome) | 1.00 | 0.23 | 0.05 | 0.02 | 1.00 | 0.45 | 0.06 | 0.03 |

[1] The amount of a recombinant CYP2D6-expressing microsome added to the reaction mixture (mg/ml).
[2] Half lives of the compounds in 60 min. incubation.
[3] Instead of a recombinant CYP2D6-expressing microsome, a control microsome which contained vector was added to the reaction mixture.

TABLE 6

T½ of P-450 substrates in CYP2C19-mediated drug metabolism

| Compounds | α-Naftoflavone | | | Nifedipine | | |
|---|---|---|---|---|---|---|
| Protein (HHM0102 + 2C19)[1] | 0 (control microsome)[3] | 0.1 | 0.3 | 0 (control microsome)[3] | 0.1 | 0.3 |
| T½[2] | 1.37 | 1.12 | 0.75 | 0.24 | 0.28 | 0.26 |
| T½ ratio (/control microsome) | 1.0 | 0.82 | 0.55 | 1.00 | 1.16 | 1.04 |

| Compounds | Imipramine | | | Yohinbine | | |
|---|---|---|---|---|---|---|
| Protein HHM0102 + 2C19[1] | 0 (control microsome)[3] | 0.1 | 0.3 | 0 (control microsome)[3] | 0.1 | 0.3 |
| T½[2] | 0.59 | 0.50 | 0.28 | 0.11 | 0.12 | 0.26 |
| T½ ratio (/control microsome) | 1.00 | 0.86 | 0.48 | 1.00 | 1.12 | 2.44 |

| Compounds | S-(+)-mephenytoin | | |
|---|---|---|---|
| Protein HM0102 + 2C19[1] | 0 (control microsome)[3] | 0.1 | 0.3 |
| T$_{1/2}$[2] | 143.4 | 4.86 | 0.46 |
| T$_{1/2}$ ratio (/control microsome) | 1.0 | 0.03 | 0.003 |

[1] The amount of a recombinant CYP2C19-expressing microsome added to the reaction mixture (mg/ml).
[2] Half lives of the compounds in 120 min incubation.
[3] Instead of a recombinant CYP2C19-expressing microsome, a control microsome which contained vector was added to the reaction mixture.

We claim:

1. A method for evaluating the susceptibility of a sample compound to metabolism by a specific cytochrome P-450 isozyme, which comprises contacting the sample compound with a reagent composition prepared by adding said specific cytochrome P-450 isozyme to a liver microsome lacking said specific cytochrome P-450 isozyme in a carrier material.

2. The method according to claim 1, which further comprises:
   (a) incubating a mixture of the sample compound and the reagent composition;
   (b) extraction of the reaction mixture obtained in Step (a); and
   (c) analyzing the reaction products isolated in Step (b).

3. The method according to claim 2, wherein a plurality of the reagent compositions having different amount of said specific P-450 are respectively subjected to Step (a) to (c).

4. The method according to claim 3, wherein said incubation is conducted at a temperature of 36.5 to 37.5° C. for a time period of 0 minute to 2 hours in a potassium phosphate buffer adjusted at pH 7.2 to 7.6.

5. The method according to claim 1, wherein said specific P-450 isozyme is CYP2D6, CYP2C19, CYP2A6, CYP1A1 or CYP2E1.

6. The method according to claim 4, wherein said specific P-450 is CYP2D6, CYP2C19, or CYP2A6.

7. A reagent composition for use in evaluating drug metabolism by a specific cytochrome P-450 isozyme, which comprises a liver microsome lacking said specific P-450, said specific P-450 isozyme and a carrier material.

8. The reagent composition according to claim 7, wherein said specific P-450 isozyme is CYP2D6, CYP2C19, CYP2A6, CYPIAI or CYP2E1.

9. The reagent composition according to claim 8, wherein said liver microsome is a human liver microsome lacking CYP2D6; and said specific P-450 isozyme is a recombinant CYP2D6-expressing microsome.

10. The reagent composition according to claim 9, wherein said human liver microsome is a CYP2D6-lacking microsome having a 1'-hydroxy bufuralol generation activity of up to 2 (pmol/min/mg) when bufuralol is used at 10 $\mu$M as a substrate.

11. The reagent composition according to claim 8, wherein said liver microsome is a human liver microsome lacking CYP2C19; and said specific P-450 isozyme is a recombinant CYP2C1 9-expressing microsome.

12. The reagent composition according to claim 11, wherein said human liver microsome is a CYP2C19-lacking microsome having a S-mephenytoin hydroxylation activity of up to 5 (pmol/min/mg) when S-mephenytoin is used at 100 $\mu$M as a substrate.

13. The reagent composition according to claim 7, which comprises 0.1 to 10 weight/volume percent of the liver microsome and 0.01 to 5.0 weight/volume percent of the specific cytochorme P-450 isozyme.

* * * * *